US006309881B2

United States Patent
Barbas et al.

(10) Patent No.: US 6,309,881 B2
(45) Date of Patent: Oct. 30, 2001

(54) ANTIBODY CATALYSIS OF ENANTIO- AND DIASTEREO-SELECTIVE ALDOL REACTIONS

(75) Inventors: Carlos F. Barbas, Del Mar; Richard A. Lerner, La Jolla; Guofu Zhong, San Diego, all of CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/824,279

(22) Filed: Apr. 2, 2001

Related U.S. Application Data

(60) Division of application No. 09/458,367, filed on Dec. 9, 1999, now Pat. No. 6,210,938, which is a continuation-in-part of application No. 09/415,453, filed on Oct. 8, 1999.

(51) Int. Cl.[7] .................................................. C12N 5/12

(52) U.S. Cl. ........................................ 435/346; 435/188.5
(58) Field of Search ................................ 435/346, 188.5

(56) References Cited

PUBLICATIONS

Evans, "Stereoselective Organic Reactions; Catalysts for Carbonyl Addition Processes", *Science 240*: 420–426 (1988).

Barbas, et al.. "Deoxyribose–5–phosphate Aldolase as a Synthetic Catalyst", *J. Am. Chem. Soc. 112*: 2013–2014 (1990).

Barbas, et al. "Assembly of Combinatorial Antibody Libraries on Phage Surfaces: The Gene III Site". *Proc. Natl. Acad. Sci. USA 88*: 7978–7982 (1991).

Janda, et al., "Direct Selection for a Catalytic Mechanism from Combinatorial Antibody Libraries", *Proc. Natl. Acad. Sci. USA 91*: 2532–2536 (1994).

Franklin, et al. "Recent Developments in Asymmetric Aldol Methodology", *Contemp. Org. Synth. 1:* 317–338 (1994).

Wong, et al.,"Enzymes in Organic Synthesis: Application to the Problems of Carbohydrate Recognition (Part I)", *Angew. Chem. Int. Ed. Engl. 34*: 412–432 (1995).

Wong, et al., "Recombinant 2–Deoxyribose–5–phosphate Aldolase in Organic Synthesis: Use of Sequential Two–Substrate and Three–Substrate Aldol Reactions", *J. Am. Chem. Soc. 117*: 3333–3339 (1995).

Carreira et al., "Catalytic, Enantioselective Acetone Aldol Additions with 2–Methoxypropene",*J. Am. Chem. Soc. 117:* 3649–3650 (1995).

Wirsching, et al., "Reactive Immunization", *Science 270:* 1775–1782 (1995).

Björnestedt, et al., "Copying Nature's Mechanism for the Decarboxylation of β–Keto Acids into Catalytic Antibodies by Reactive Immunization", *J. Am. Chem. Soc. 118:* 11720–11724 (1996).

Zhong, et al., "Antibody–Catalyzed Enantioselective Robinson Annulation", *J. Am. Chem. Soc. 119:* 8131–8132 (1997).

(List continued on next page.)

Primary Examiner—Charles L. Patterson, Jr.
(74) Attorney, Agent, or Firm—Thomas E. Northrup

(57) ABSTRACT

Nine efficient aldolase antibodies were generated using hapten 2. This hapten combines, in a single molecule, structural components employed for reactive immunization with structural components employed for forming a transition state analog of the aldol reaction. Characterization of two of these antibodies reveals that they are highly proficient (up to 1000-fold better than any other antibody catalyst) and enantioselective catalysts for aldol and retro-aldol reactions and exhibit enantio- and diastereo-selectivities opposite that of antibody 38C2.

6 Claims, 4 Drawing Sheets

OTHER PUBLICATIONS

Barbas, et al., "Immune Versus Natural Selection: Antibody Aldolases with Enzymic Rates but Broader Scope", *Science 278:* 2085–2092 (1997).

Hoffmann, et al., "Aldolase Antibodies of Remarkable Scope", *J. Am. Chem. Soc. 120:* 2768–2779 (1998).

Zhong, et al., "Catalytic Enantioselective Retro–Aldol Reactions: Kinetic Resolution of β–Hydroxyketones with Aldolase Antibodies", *Angew. Chem. Int. Ed. Engl. 37:* 2481–2484 (1998).

List, et al., "Enantioselective Total Synthesis of Some Brevicomins Using Aldolase Antibody 38C2", *Chem. Eur. J. 4:* 881–885 (1998).

Sinha, et al., "The Antibody Catalysis Route to the Total Synthesis of Epothilones", *Proc. Natl. Acad. Sci. USA 95:* 14603–14608 (1998).

List, et al., "Aldol Sensors for the Rapid Generation of Tunable Fluorescence by Antibody Catalysis", *Proc. Natl. Acad. Sci. USA 95:* 15351–15355 (1998).

| product | | conversion | ee |
|---|---|---|---|
|  | (S-3) | 51 % | 99 %[a] |
|  | (S-4) | 50 % | 97 %[a] |
|  | (S-5) | 52 % | > 99 %[a,b] |
|  | (S-6) | 50 % | 96 %[a] |
|  | (S-7) | 50 % | > 99 %[b] |

| product[a] | | ee[b] |
|---|---|---|
|  | (R-5) | > 99 % |
|  | (S-8) | 69 % |
|  | (R-9) | 95 % |
|  | (R-10) | 98 % |
|  | (S,R-11) | 90 % (syn/anti =95:5) |

| Substrate | Antibody | $k_{cat}$[a,b] [min$^{-1}$] | $K_m$[a,b] [mM] | $k_{cat}/k_{un}$[c] | $(k_{cat}/K_m)/k_{un}$[d] |
|---|---|---|---|---|---|
| (±) -3 | 93F3 | 2.65 | 15 | 2.7 x 10$^6$ | 1.8 x 10$^{11}$ |
|  | 84G3 | 3.5 | 23 | 3.6 x 10$^6$ | 1.6 x 10$^{11}$ |
|  | 38C2[e] | 1.0 | 14 | 1.0 x 10$^6$ | 7.1 x 10$^{10}$ |
| (±) -4 | 93F3 | 0.50 | 40 | 2.7 x 10$^3$ | 6.6 x 10$^7$ |
|  | 84G3 | 0.43 | 45 | 2.4 x 10$^3$ | 5.9 x 10$^7$ |
|  | 38C2[f] | 4.7 | 41 | 2.6 x 10$^4$ | 6.4 x 10$^8$ |
| (±) -5 | 84G3 | 0.95 | 17 | 4.3 x 10$^4$ | 2.7 x 10$^9$ |
|  | 38C2[f] | 2.2 | 16 | 1.0 x 10$^5$ | 6.3 x 10$^9$ |
| (±) -7 | 93F3 | 43.3 | 6.5 | 4.9 x 10$^7$ | 7.4 x 10$^{12}$ |
|  | 84G3 | 46.8 | 10.3 | 5.2 x 10$^7$ | 5.0 x 10$^{12}$ |
|  | 38C2 | 0.053 | 29.5 | 5.8 x 10$^4$ | 2.0 x 10$^9$ |
| (R) -16 | 93F3 | 69.6 | 2.6 | 1.9 x 10$^8$ | 7.4 x 10$^{13}$ |
|  | 84G3 | 81.4 | 4.2 | 2.3 x 10$^8$ | 5.4 x 10$^{13}$ |
| 11 & acetone | 93F3 | 33 x 10$^{-3}$ | 34 | 1.5 x 10$^5$ | 4.4 x 10$^9$ |
|  | 84G3 | 27 x 10$^{-3}$ | 29 | 1.2 x 10$^5$ | 4.1 x 10$^9$ |
|  | 38C2[g] | 6.7 x 10$^{-3}$ | 17 | 2.9 x 10$^4$ | 1.7 x 10$^9$ |
| 13 & acetone | 93F3 | 0.22 | 197 | 6.9 x 10$^5$ | 3.5 x 10$^9$ |
|  | 84G3 | 0.14 | 210 | 4.4 x 10$^5$ | 2.1 x 10$^9$ |
|  | 38C2 | 0.11 | 214 | 3.4 x 10$^5$ | 1.6 x 10$^9$ |
| 12 & 3-pentanone | 93F3 | 1.7 x 10$^{-2}$ | 132 | 7.5 x 10$^4$ | 5.7 x 10$^8$ |
|  | 38C2[g] | 0.5 x 10$^{-2}$ | 115 | 2.1 x 10$^4$ | 1.8 x 10$^8$ |

Figure 6

ANTIBODY CATALYSIS OF ENANTIO- AND DIASTEREO-SELECTIVE ALDOL REACTIONS

CROSS-REFERENCE TO RELATED APPLICATIONS

This is a divisional application of application Ser. No. 09/458,367, filed Dec. 9,1999, now U.S. Pat. No. 6,210,938, which is a continuation-in-part of application Ser. No. 09/415,453, filed Oct. 8, 1999.

STATEMENT OF GOVERNMENT RIGHTS

This invention was made with government support under the National Cancer Institute grant No. CA 27489. The U.S. government has certain rights in the invention.

FIELD OF THE INVENTION

The invention relates to antibody catalyzed aldol reactions. More particularly the invention relates to enantio- and diastereo-selective aldol reactions and to antibodies that catalyzed such reactions.

BACKGROUND

The aldol reaction is a C—C bond forming reaction that is key to the practice of synthetic organic chemistry. For reviews of the aldol reaction, see: a) S. Masamune, et al., Angew. Chem. Int. Ed. Engl. 1985, 24, 1–30; b) C. H. Heathcock, Aldrichim. Acta 1990, 23, 99–111; c) D. A. Evans, Science 1988, 240, 420–426; d) C. H. Heathcock, et al, in Comprehensive Organic Synthesis, Vol. 2 (Eds. B. M. Trost, I. Fleming, C. H. Heathcock), Pergamon, Oxford, 1991, pp. 133–319; e) C. J. Cowden, et al., Org. React. 1997, 51, 1; f) A. S. Franklin, et al., Contemp. Org. Synth. 1994, 1, 317. As a result of its utility, intensive effort has been applied to the development of catalytic enantioselective variants of this reaction. Catalytic enantioselective aldol reactions are typically accomplished with preformed enolates and chiral transition metal catalysts (S. G. Nelson, Tetrahedron: Asymmetric 1998, 9, 357–389; A. Yanagisawa, et al., J. Am. Chem. Soc. 1997, 119, 9319–9320; E. M. Carreira, et al., J. Am Chem. Soc. 1995, 117, 3649–3650; D. A. Evans, et al., J. Am. Chem. Soc. 1997, 119, 10859–10860; and D. J. Ager, et al., Asymmetric Synthetic Methodology (CRC Press, Inc.: Florida, 1996). Alternatively, catalytic enantioselective aldol reactions may be achieved with natural aldolase enzyme catalysts (C.-H. Wong, et al., Enzymes in Synthetic Organic Chemistry (Pergamon, Oxford, 1994); C.-H. Wong, et al., Angew. Chem. Int. Ed. Engl. 1995, 34, 412–432; and W.-D. Fessner, Current Opinion in Chemical Biology 1998, 2, 85–89). With transition metal catalyzed aldol reactions, enantioselectivity is readily reversed by exchange of the chiral ligand that directs the stereochemical course of the reaction. With enzymes, however, a general approach to the reversal of enantioselectivity is not available.

To address the problem of the de novo generation of aldolase enzymes, a strategy of reactive immunization using β-diketone haptens to program into antibodies a chemical mechanism analogous to that used by nature's Class I aldolase enzymes was developed. The chemistry of this class of enzymes is based on a unique chemically reactive lysine residue that is essential to the covalent mechanism of these catalysts. FIG. 1 illustrates a prior art hapten, viz., compound 1, having a β-diketone functionality employable as a reactive immunogen capable of trapping a chemically reactive lysine residue in the active site of an antibody. Covalent trapping was facilitated by intramolecular hydrogen bonding that acts to stabilize an enaminone in the active site of the antibody. The chemical mechanism leading up to the stabilized enaminone should match that of Class I aldolases over this portion of the reaction coordinate. Given the mechanistic symmetry around the C—C bond forming transition state, this approach allowed for the programming of this multi-step reaction mechanism into antibodies (C. F. Barbas III, et al., Science 1997, 278, 2085–2092). The efficient antibody catalysts that resulted, ab38C2 (Aldrich reagent) and ab33F12 have been shown to catalyze a broad array of enantioselective aldol and retro-aldol reactions (R. Bj örnestedt, et al., J. Am. Chem. Soc. 1996, 118, 11720–11724; G. Zhong, et al., J. Am. Chem. Soc. 1997, 119, 8131–8132; T. Hoffmann, et al., J. Am. Chem. Soc. 1998, 120, 2768–2779; and S. C. Sinha, et al., J. Am. Chem. Soc. 1999, submitted). For an alternative aldolase antibody strategy see J. L. Reymond, Angew. Chem. Int. Ed. Engl. 1995, 34, 2285–2287 or J. L. Reymond, et al., J. Org. Chem 1995, 60, 6979.

What is needed is a method for increasing the repertoire of catalysts for this reaction. In particular, antibodies with antipodal reactivity are needed. What is needed is a new hapten design concept for providing more efficient reaction programming.

SUMMARY

It is disclosed herein that a limitation of the design of prior art hapten 1 is that it does not address the tetrahedral geometry of the rate-determining transition state of the C—C bond forming step (J. Wagner, et al., Science 1995, 270, 1797–1880). For discussions of the transition state geometry of the aldol reaction, see: a) H. E. Zimmerman, et al., J. Am. Chem. Soc. 1957, 79, 1920; b) S. E. Denmark, et al., J. Am. Chem. Soc. 1991, 113, 2177–2194 and references therein; c) C. Gennari, et al., Tetrahedron 1992, 48, 4439–4458.

Illustrated in FIG. 1 is a novel sulfone β-diketone hapten, viz., compound 2, which overcomes this limitation by containing structural features common to the transition state analog approach that has been successful for so many reactions (P. G. Schultz and R. A. Lerner, Science 1995, 269, 1835–1842; and N. R. Thomas, Nat. Prod. Rep. 1996, 13, 479–511). The sulfone β-diketone hapten 2 also includes the β-diketone functionality, which is key to the reactive immunization strategy. The tetrahedral geometry of the sulfone moiety in hapten 2 mimics the tetrahedral transition state of C—C bond forming step and therefore facilitates nucleophilic attack of the enaminone intermediate on the acceptor aldehyde (FIG. 2).

It is disclosed herein that combining transition state analogy and reactive immunization design into a single hapten results in an increase with respect to both the output of catalysts from the immune system as well as their efficiency as catalysts. This strategy resulted in the characterization of the most proficient antibody catalysts prepared to date. Antibodies 93F3 and 84G3 catalyze a wide array of aldol reactions with ee's in most cases studied exceeding 95%. With acetone as the aldol donor substrate a new stereogenic center is formed by attack on the re-face of the aldehyde, providing the antipodal complement of ab38C2 in aldol reactions. Through aldol and retro-aldol reactions both aldol enantiomers may be accessed. These catalysts are shown to provide access to a wide variety of enantiomerically enriched synthons with application to natural product syntheses.

One aspect of the invention is directed to a hapten that combines a structure that mimics a transition state of an aldol reaction as found in Class I aldolases together with a structure employable in a reactive immunization. In a preferred embodiment, the hapten is represented by the following structure:

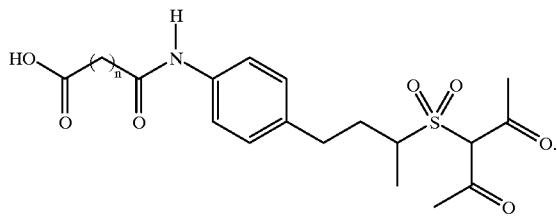

In the above structure, n is greater than or equal to 2 and less than or equal to 8. Alternatively, n may be greater than or equal to 4 and less than or less than or equal to 6. In a preferred embodiment, n is five.

Another aspect of the invention is directed to a transition state immunoconjugate represented by the following structure:

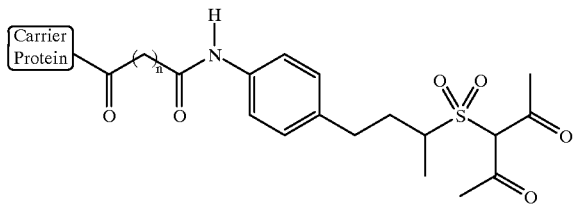

In the above structure, n is greater than or equal to 2 and less than or equal to 8; alternative, n may be greater than or equal to 4 and less than or equal to 6; or alternatively, n is five. A preferred carrier protein is keyhole limpet hemocyanin (KLH).

Another aspect of the invention is directed to a process for producing a catalytic monoclonal antibody for catalyzing an aldol reaction. In the first step of the process, an immune response is elicited within an immune responsive subject by injecting a sterile solution of a hapten-carrier protein. The hapten-carrier protein is of a type which includes a sulfone β-diketone hapten. In a preferred mode, the hapten-carrier protein is represented by the following structure:

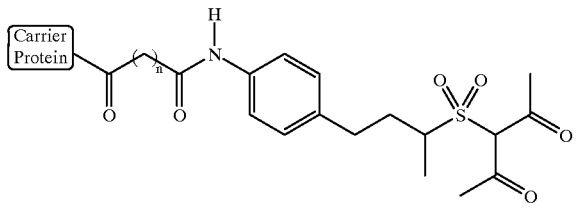

Then, an antibody producing cell which expresses a catalytic antibody for catalyzing the aldol reaction is isolated and cloned from the immune responsive subject. And then, aldolase catalytic antibody is isolated as it is expressed by the antibody producing cell isolated and cloned in the previous step.

Another aspect of the invention is directed to antibody molecules or molecules containing antibody combining site portions that catalyze an aldol addition reaction. The antibody molecules or molecules containing antibody combining site portions are produced by eliciting an aldolase immune response within an immune response subject by vaccination with a sterile solution containing the appropriate concentration of an aldol transition state immunoconjugate. The aldol transition state immunoconjugate is of the type which includes a sulfone β-diketone hapten. In a preferred mode, the hapten-carrier protein is represented by the following structure:

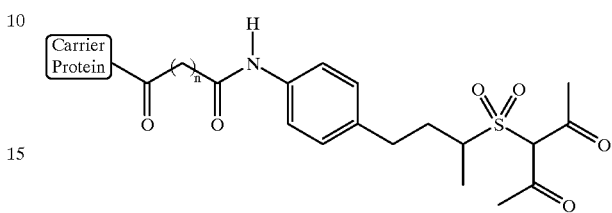

Then, an antibody producing cell which expresses a catalytic antibody for catalyzing the aldol reaction is isolated and cloned from the immune responsive subject. And then, aldolase catalytic antibody is isolated as it is expressed by the antibody producing cell isolated and cloned in the previous step. Preferred antibody molecules or molecules containing antibody combining site portions include hybridoma 85A2, having ATCC accession number PTA-1015; hybridoma 85C7, having ATCC accession number PTA-1014; hybridoma 92F9, having ATCC accession number PTA-1017; hybridoma 93F3, having ATCC accession number PTA-823; hybridoma 84G3, having ATCC accession number PTA-824; hybridoma 84G11, having ATCC accession number PTA-1018; hybridoma 84H9, having ATCC accession number PTA-1014; hybridoma 85H6, having ATCC accession number PTA-825; hybridoma 90G8, having ATCC accession number PTA-1016.

Another aspect of the invention is directed to an antibody producing cell which secretes antibody molecules or molecules containing antibody combining site portions that catalyze an aldol addition reaction. The antibody producing cell is produced by eliciting an aldolase immune response within an immune response subject by vaccination with a sterile solution containing the appropriate concentration of the aldol transition state immunoconjugate, The aldol transition state immunoconjugate includes a sulfone β-diketone hapten. In a preferred mode, the aldol transition state immunoconjugate is represented by the following structure:

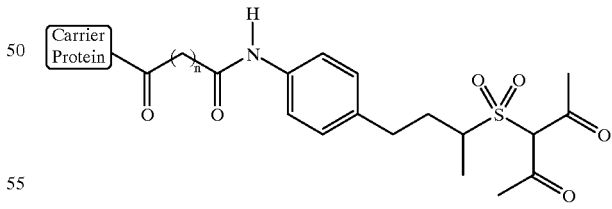

Then, an antibody producing cell which expresses a catalytic antibody for catalyzing the aldol reaction is isolated and cloned from the immune responsive subject and converted to a hybridoma. Preferred hybridomas include hybridoma 85A7, having ATCC accession number PTA-1615; hybridoma 85C7, having ATCC accession number PTA-1014; hybridoma 92F9, having ATCC accession number PTA-1017; hybridoma 93F3, having ATCC accession number PTA-823; hybridoma 84G3, having ATCC accession number PTA-874; hybridoma 84G11, having ATCC accession number PTA-1018; hybridoma 84H9, having ATCC accession number PTA-1019; hybridoma 85H6, having ATCC accession number PTA-825; hybridoma 90G8, having ATCC accession number PTA-1016.

Another aspect of the invention is directed to an improved kinetic resolution of β-hydroxyketones from a racemic mixture by means of a retro-aldo reaction using the catalytic monoclonal antibodies for catalyzing aodol reactions described herein.

Another aspect of the invention is directed to an improved process for catalyzing an aldol reaction between aldehyde and ketone reactants. In the improved process, the aldehyde and ketone reactants are contacted with antibody molecules or molecules containing antibody combining site portions that catalyze an aldol addition reaction. The antibody molecules or molecules containing antibody combining site portions are produced by eliciting an aldolase immune response within an immune response subject by vaccination with a sterile solution containing the appropriate concentration of an aldol transition state immunoconjugate. The aldol transition state immunoconjugate includes a sulfone β-diketone hapten. In a preferred mode, the hapten-carrier protein is represented by the following structure:

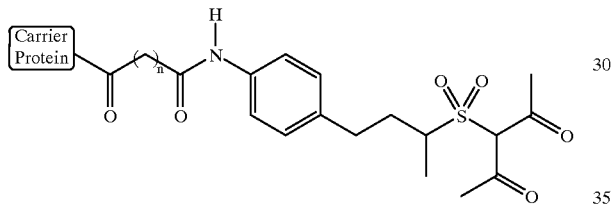

Then, an antibody producing cell which expresses a catalytic antibody for catalyzing the aldol reaction is isolated and cloned from the immune responsive subject. And then. aldolase catalytic antibody is isolated as it is expressed by the antibody producing cell isolated and cloned in the previous step. Preferred antibody molecules or molecules containing antibody combining site portions include hybridoma 85A2, having ATCC accession number PTA-1018; hybridoma 85C7, having ATCC accession number PTA-1014; hybridoma 92F9, having ATCC accession number PTA-1017; hybridoma 93F3, having ATCC accession number PTA-823; hybridoma 84G3, having ATCC accession number PTA-824; hybridoma 84G11, having ATCC accession number PTA-1018; hybridoma 84H9, having ATCC accession number PTA-1019; hybridoma 85H6, having ATCC accession number PTA-825; hybridoma 90G8, having ATCC accession number PAT-1016. Preferred ketones include the following compounds:

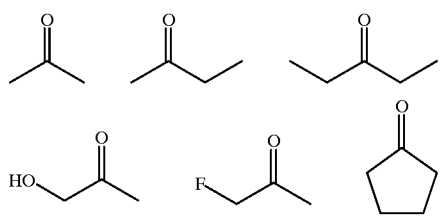

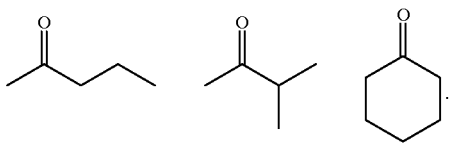

Preferred aldehydes include the following compounds:

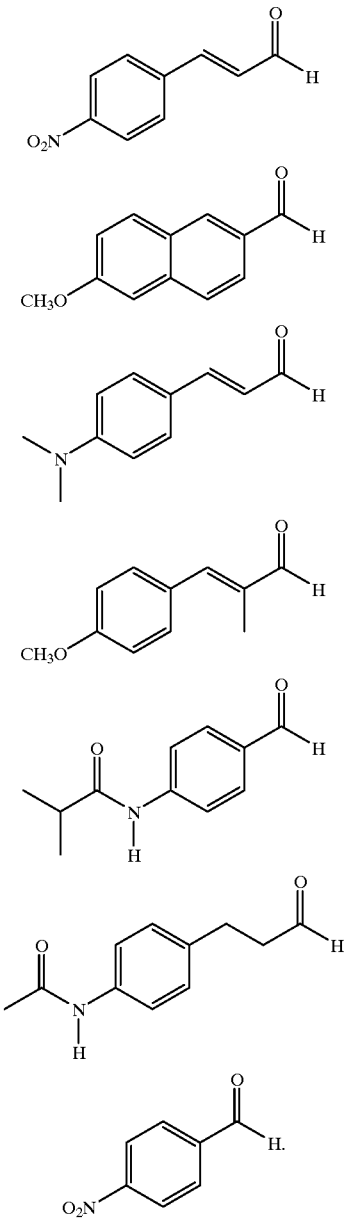

In a preferred mode, the antibody molecules are selected from a group consisting of 85A2, 85C7, 92F9, 93F3, 84G3, 84G11, 84H9, 85H6 and 90G8.

BRIEF DESCRIPTION OF FIGURES

FIG. 6 illustrates a table illustrating kinetic parameters for additional antibody catalyzed aldol and retro-aldol reactions. a, Conditions: All data was determined in phosphate buffered saline (PBS) at pH 7.4. [b] Per antibody active site. $k_{cat}$ and $K_m$ were obtained by fitting experimental data to non-linear regression analysis using Grafit software. [c] Aldol reactions with a unit [M]. [d] Retro-aldol reactions with a unit [M$^{-1}$]. [e] B. List, et al., *Proc. Natl. Acad. Sci. USA* 1998, 95, 15351–15355. [f] G. Zhong,, et al., *Angew. Chem. Int. Ed. Engl.* 1998, 37, 2481–2484. [g] J. Wagner, et al., *Science* 1995, 270, 1797–1880.

DETAILED DESCRIPTION

Figure 1:
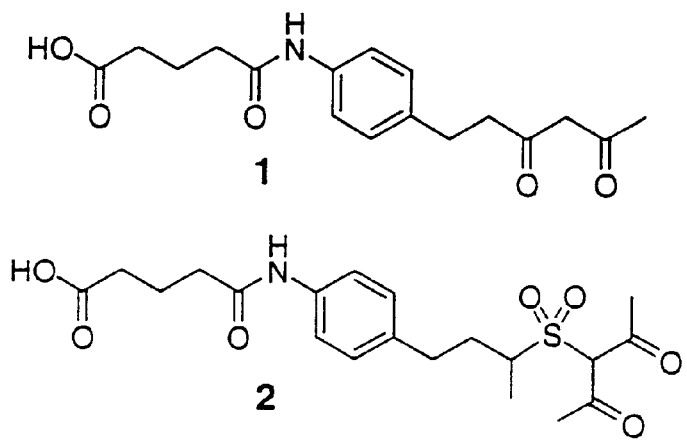
FIG. 1 illustrates both the prior art hapten (compound 1) and the claimed hapten (compound 2). Both haptens are employable for the generation of aldolase antibodies.
Figure 2:
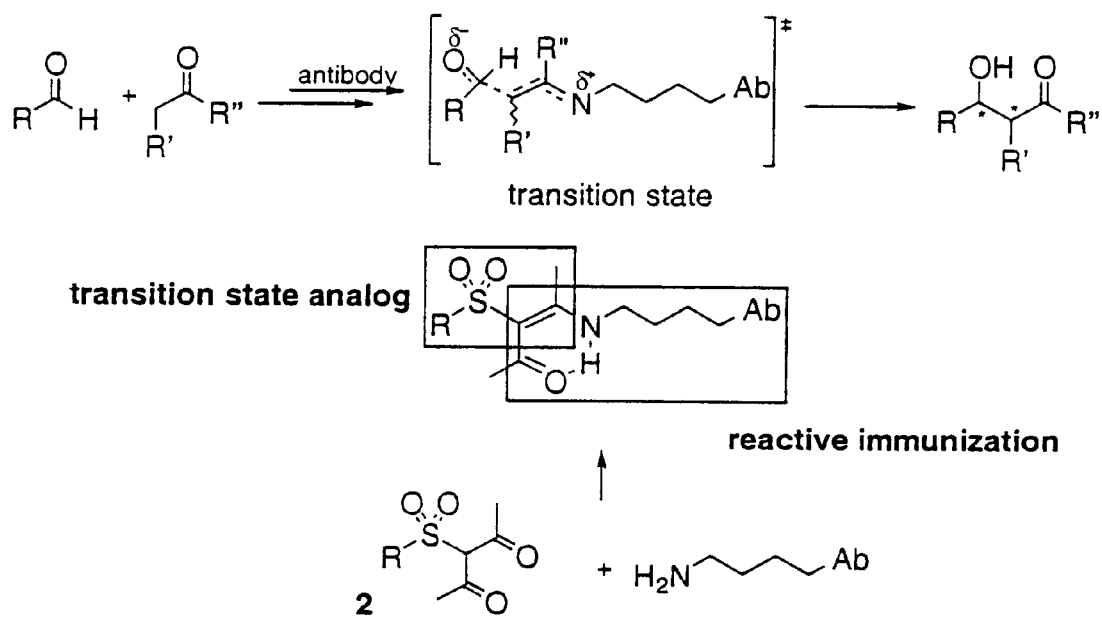
FIG. 2 illustrates the mechanism of antibody catalyzed aldol reaction and reactive immunization with hapten 2 for the generation of new aldolase antibodies. The transition state formed during the aldol reaction and the transition state analog formed during reactive immunization are juxtaposed so as to illustrate their structural similarity.
Figure 3:
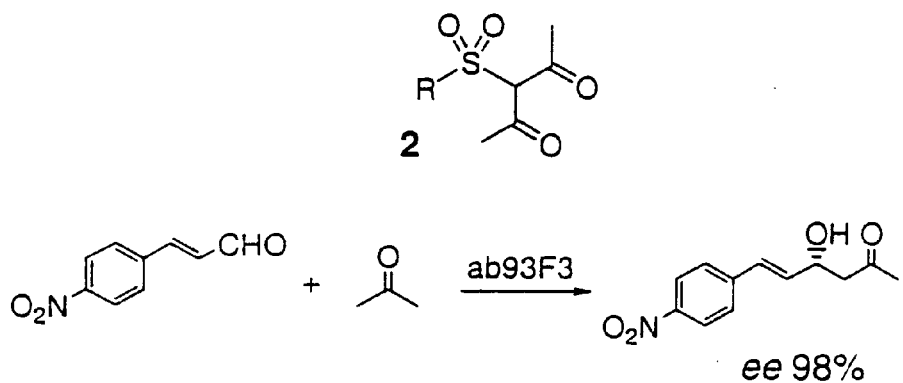
FIG. 3 illustrates an antibody 93F3 catalyzed aldol reaction. Antibody 93F3 was formed by reactive immunization using hapten 2.

Mice were immunized with the sulfone β-diketone hapten 2 coupled to the carrier protein keyhole limpet hemocyanin (KLH) and 17 monoclonal antibodies were prepared and purified as described. All antibodies were first screened for their ability to covalently react with 2,4-pentanedione to form a stable enaminone (UV at $\lambda_{max}$ 316 nm) (J. Wagner, et al., *Science* 1995,270, 1797–1880). Nine antibodies, 85A2, 85C7, 92F9, 93F3, 84G3, 84G11, 84H9, 85H6 and 90G8, showed the characteristic enaminone absorption maximum at 316 nm after incubation with 2,4-pentanedione. All antibodies were then assayed with fluorescent and UV active retro-aldol substrates (±)-3 and (±)-4, respectively (B. List, et al., *Proc. Natl. Acad. Sci. USA* 1998, 95, 15351–15355; and G. Zhong, et al., *Angew. Chem Int. Ed. Engl.* 1998, 37, 2481–2484). Catalysis was observed only with antibodies that had demonstrated enaminone formation with 2,4-pentanedione. Study of all antibodies for their ability to catalyze the aldol addition of acetone to the aldehydes, 3-(4'-acetamidophenyl)propanal (12) and 4-isobutyramidobenzaldehyde (13), identified the same catalysts. All antibody catalyzed aldol and retro-aldol reactions followed Michaelis-Menten kinetics and were inhibited by addition of a stoichiometric amount of 2,4-pentanedione. These results are consistent with the programming of a reactive amine in covalent catalytic mechanism of these antibodies. The output of catalysts prepared using this hapten, 9 of 17, is significantly greater than previous studies with hapten 1 where 2 of 20 antibodies were catalysts.

Deposit of Hybridomas

Deposits for hybridoma 84G3, having ATCC accession number PTA-824, for hybridoma 85H6, having ATCC accession number PTA-825, for hybridoma 93F3, having ATCC accession number PTA-823, for hybridoma 85A2, having ATCC accession number PTA-1015, for hybridoma 85C7, having ATCC accession number PTA-1014, for hybridoma 92F9, having ATCC accession number PTA-1017, for hybridoma 84G11, having ATCC accession number PTA-1018, for hybridoma 84H9, having ATCC accession number PTA-1019, and for hybridoma 90G8, having ATCC accession number PTA-1016, were made in compliance with the Budapest Treaty requirements that the duration of the deposits should be for 30 years from the date of deposit at the depository or for the enforceable life of a U.S. patent that matures from this application, whichever is longer. The hybridoma cell lines will be replenished should any of them become non-viable at the depository, under the terms of the Budapest Treaty, which assures permanent and unrestricted availability of the progeny of the hybridomas to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 CFR §1.14 with particular reference to 886 OG 638). The assignee of the present application has agreed that if the hybridoma deposit should die or be lost or destroyed when cultivated under suitable conditions, it will be promptly replaced on notification with a viable specimen of the same hybridoma. Availability of the deposit is not to be construed as a license to practice the invention in contravention of the rights granted under the authority of any government in accordance with its patent laws.

In order to compare these antibodies with the commercially available aldolase antibody 38C2, several aldol and retro-aldol reactions were chosen for study. In these studies, antibodies 93F3 and 84G3 were characterized in detail.

Scope and Synthetic Utility

Figure 4:
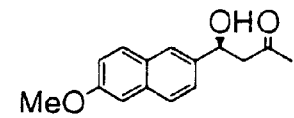
FIG. 4 is a table illustrating antibody 93F3 and 84G3 catalyzed kinetic resolutions by retro-aldolization. [A] Antibody 93F3 was used. Absolute configurations assigned by comparing aldol products with those obtained from ab38C2 catalyzed reactions. [B] Antibody 84G3 was used.
Figure 4:
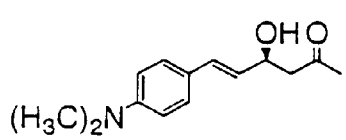
Figure 4:
Figure 4:
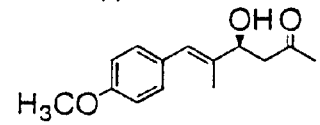
Figure 4:
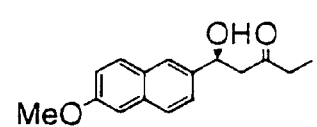

To begin to probe the synthetic scope and enantioselectivity of these antibodies, their utility for kinetic resolutions of β-hydroxyketones was characterized. Racemic aldols 3–7 were treated with (0.2–0.4 Mol %) ab93F3 (or ab84G3) in aqueous buffer as previously described for ab38C2 (G. Zhong, et al.. *Angew. Chem. Int. Ed. Engl.* 1998, 37, 2481–2484). In each case high-performance liquid chromatography (HPLC) indicated that the retro-aldolization reactions halted at ~50% conversion showing that the antibody was highly enantioselective. The unconverted aldols were recovered and studied using chiral-phase HPLC. Comparison with enantiomerically-enriched standards, according to the method of I. Paterson, et al., *Tetrahedron* 1990, 46, 4663–4684, indicated that the catalyst was highly enantioselective and provided the unreacted S-aldols with ee's typically greater than 96% (FIG. 4). Antibody 38C2 provides the corresponding R-aldols by kinetic resolution, thus ab93F3 is its antipodal complement. Study of ab84G3 revealed an enantioselectivity similar to ab93F3 and identified two catalysts with enantioselectivities similar to ab38C2.

Figure 5:
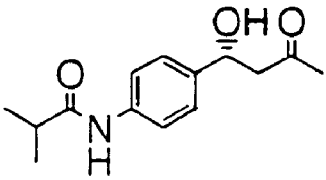
FIG. 5 is a table illustrating antibody 93F3 catalyzed aldol reactions. a, Absolute configurations assigned by asymmetric synthesis of the aldols (I. Paterson, et al., *Tetrahedron* 1990, 46, 4663–4684). b, Antibody 93F3 was used in all reactions.
Figure 5:
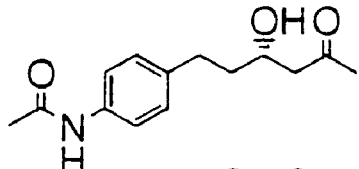
Figure 5:
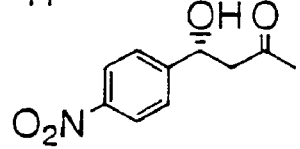
Figure 5:
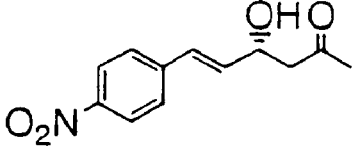
Figure 5:
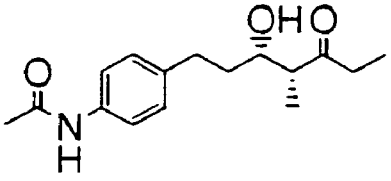

Catalysis of the synthetic reaction of acetone was then characterized with four different aldehydes, 12, 13, 4-nitrobenzaldehyde (14) and 4-nitrocinnamaldehyde (15), to provide aldols 5 and 8–10. Chiral-phase HPLC analysis demonstrated that the enantioselectivities of ab93F3 and ab84G3 catalyzed aldol addition reactions are substrate dependant. Aldols R-5, R-9 and R-10 are provided in essentially enantiomerically pure form with either catalyst while a moderate enantioselectivity is obtained in the synthesis of S-8 (ee 69% with ab93F3 or 54% with ab84G3)(see FIG. 5). The ee values obtained with these catalysts are quite similar to those obtained with ab38C2, however, the enantioselectivity is reversed.

To examine the diastereoselectivity of ab93F3, the reaction of 3-pentanone to provide aldol-11 was characterized. In this case ab93F3 provided aldol syn-11 as the major product. The antibody 93F3 exhibited diastereo- and enantio-selectivities that differ from that obtained with ab38C2. Antibody 93F3 provides 11 with a de of 90% (syn-α-isomer) and an ee of 90% while ab38C2 provides 11 with a de of 62% (anti-isomer) and an ee of 59%.

To further characterize the scope of reactions catalyzed by these antibodies, a variety of ketones were employed as aldol donor substrates in reaction with aldehyde 14. Preliminary results indicate that in addition to acetone and 3-pentanone, seven ketones: 2-butanone, 3-methyl-2-butanone, 2-pentanone, cyclopentanone, cyclohexanone, hydroxyacetone, and fluoroacetone, are substrates. Thus these antibodies share the characteristic broad scope observed previously with ab38C2.

Kinetic Studies

The results of kinetic studies of three retro-aldol reactions and one aldol addition reaction are provided (FIG. 6). In most cases studied, the catalytic proficiency of ab93F3 and ab84G3 exceeds that of ab38C2, as determined by the method of A. R. Radzicka, et al., *Science* 1995, 267, 90–93. In the aldol reaction of acetone with aldehyde 12 that provides S-8, a 3-fold increase in the catalytic proficiency is observed. An overall trend towards increased efficiency is consistent with the notion that inclusion of transition state analogy into the hapten design results in increased catalytic efficiency. This effect is particularly evident with substrate 7 where a $10^3$-fold increase in proficiency over ab38C2 is observed. Based on the success of this substrate, analog 16 was synthesized.

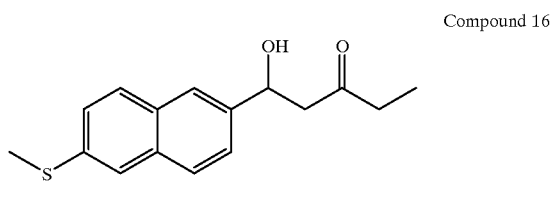

Compound 16

Since in antibody based resolutions of aldols, the unprocessed enantiomer can be inhibitory to the processing of the enantiomer that is the substrate for the antibody (B. List, et al., *J. Am. Chem. Soc.* 1999, 121, in press), R-16 was isolated using chiral-phase HPLC. Study of the kinetics of retro-aldolization of R-16 by ab84G3, revealed that it was processed by the antibody extremely rapidly with a $k_{cat}$ of $1.4\ s^{-1}$. Study of the uncatalyzed reaction revealed that R-16 was not more chemically reactive than the corresponding methoxy derivative 7, and that the antibody provides a rate enhancement $k_{cat}/k_{un}$ of $2.3 \times 10^8$. The catalytic proficiency of ab84G3 for the retro-aldolization of aldol R-16 is approximately 1000-fold higher than that reported for any other catalytic antibody (N. R. Thomas, *Appl. Biochem. Biotechnol.* 1994, 47, 345–72; and G. Zhong, et al., *Angew. Chem. Int. Ed. Engl.* 1998, 37, 2481–2484). The catalytic efficiency of the antibody for this substrate, $3.3 \times 10^5\ s^{-1}M^{-1}$, compares favorably with the efficiency of nature's muscle aldolase, $4.9 \times 10^4\ s^{-1}M^{-1}$, in the retro-aldolization of its substrate fructose-1,6-bisphosphate (A. J. Morris, et al., *Biochemistry* 1994, 33, 12291–12297, data for muscle aldolase was reported at 4° C.).

Scheme 1
Preparation of the Hapten for Aldolase Antibodies

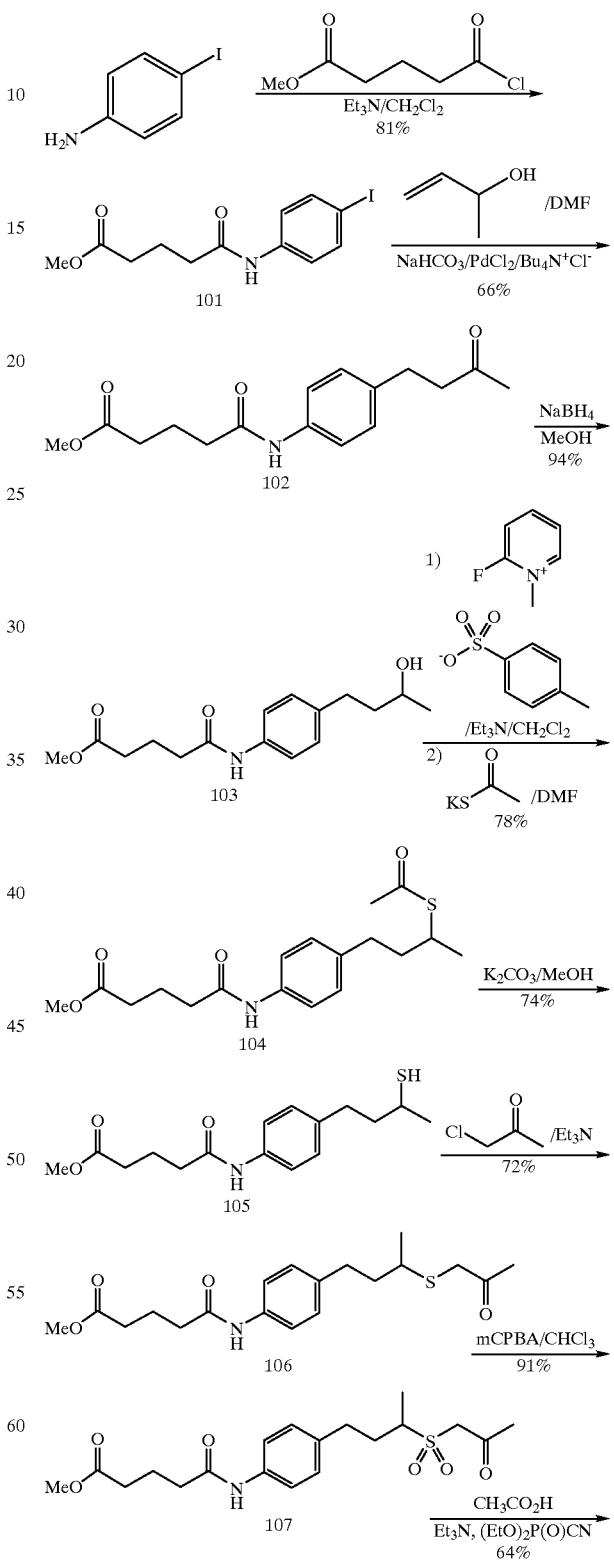

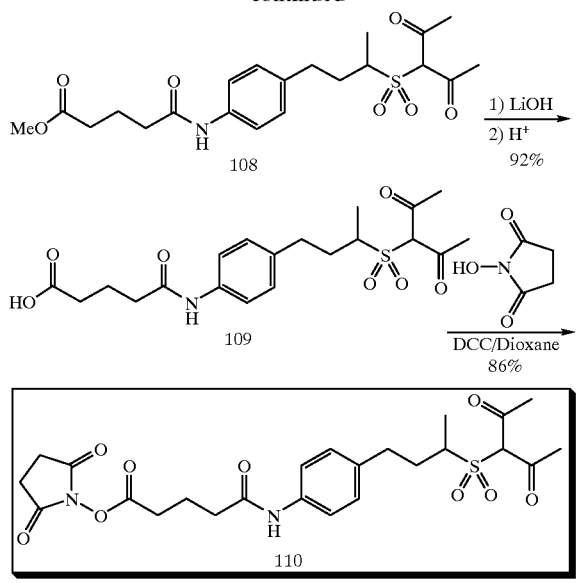

1. 4-(4'-Iodophenylcarbamoyl)butyric acid methyl ester (101): 4Iodophenylamine (6.0 g, 27 mmol) was dissolved in 240 mL of dried methylene chloride. Triethylamine (3.9 mL, 27 mmol) was added. Methyl 4chloroformyl)butyrate (4.2 mL, 28 mmol) was added dropwise. After 30 min of standing, the reaction mixture was washed with 50 mL of aqueous HCl (0.5 M). The organic phase was dried over magnesium sulfate. Evaporation of solvent gave 8.3 g, of the ester (101) for a yield 81%.

2. 4-[4'-(3"-Oxobutyl)phenylcarbamoyl]butyric acid methyl ester (102): 4(4'-iodophenylcarbamoyl)butyric acid methyl ester (4.9 g, 14 mmol) was added to 16 mL of dried DMF, then tetrabutylammonium chloride (3.9 g, 14 mmol), sodium bicarbonate (2.9 g, 35 mmol) and 3-buten-2-ol (21 mmol) were added. The mixture was stirred for 10 min. Then palladium chloride (0.57 g, 3.2 mmol) was added. The reaction mixture was kept stirring at room temperature for 24 h under nitrogen. It was diluted with 120 mL of ethyl acetate, washed with 25 mL of 5% hydrochloric acid and 2×25 mL of brine and dried over magnesium sulfate. Evaporation of solvent gave crude product, which was purified by column chromatography on silica gel (ethyl acetate/hexane: 70/30), 2.7 g of pure 4-[4'-(3"-oxobutyl)phenylcarbamoyl] butyric acid methyl ester (102) was obtained for a yield of 66%.

3. 4-[4'-(3"-Hydroxybutyl)phenylcarbamoyl)butyric acid methyl ester (103): At 0° C., sodium borohydride (0.22 g, 3 mmol) was added in portions to 4-[4'-(3"-oxobutyl) phenylcarbamoyl]butyric acid methyl ester (1.6 g, 5.6 mmol) in 25 mL of dried methanol. The reaction mixture was kept at 0° C. for 1 h. Then it was poured into 200 mL of ammonium chloride saturated ice-water. It was extracted with 3×100 mL of ethyl acetate. The combined organic phases were dried over sodium sulfate. Evaporation of the solvent gave 1.5 g of 4-[4'-(3"-hydroxybutyl) phenylcarbamoyl]butyric acid methyl ester (103) with a yield 94%.

4. 4-[4'-(3"-Acetylsulfanylbutyl)phenylcarbamoyl]butyric acid methyl ester (104): 4-4'-(3"-Hydroxybutyl) phenylcarbamoyl]butyric acid methyl ester (200 mg, 0.68 mmol) was dissolved in 6 mL of dry methylene chloride. Triethylamine (140 µL, 1.02 mmol) was added. In a second flask, 2-fluoro-1-methylpyridinium p-toluenesulfonate (250 mg, 0.88 mmol) was suspended in 6 mL of dry methylene chloride. The above solution was added to 4-[4'-(3"-hydroxybutyl)phenylcarbamoyl]butyric acid methyl ester in dry methylene chloride and stirred for 1 h. The solvent was evaporated and the residue was dissolved in 6 mL of dry DMF. Potassium thioacetate was added and heated to 80° C. for one and a half hours. The reaction mixture was diluted with 80 mL of ethyl acetate and washed with 2×20 mL of water. The organic phases were dried over magnesium sulfate. Evaporation of solvent followed by column chromatography (methylene chloride/diethyl ether: 1:3) to afford yellowish product (104) (186 mg, yield 78%).

5. 4-[4'-(3"-Mercaptobutyl)phenylcarbamoyl]butyric acid methyl ester (105): 4-[4'-(3"-acetylsulfanylbutyl) phenylcarbamoyl]butyric acid methyl ester (165 mg, 0.47 mmol) was dissolved in 4 mL of methanol. Potassium carbonate (6.5 mg, 0.047 mmol) was added. The mixture was stirred for 3 h. The solvent was evaporated and the residue was purified by column chromatography (methylene chloride/diethyl ether: 1:3) to afford 4- [4'-(3"-mercaptobutyl)phenylcarbamoyl]butyric acid methyl ester (105) (110 mg, yield 74%).

6. 4-{4'-[3"-(2'"-Oxopropylsulfanyl)butyl] phenylcarbamoyl}butyric acid methyl ester (106): 4-[4'-(3"-mercaptobutyl)phenylcarbamoyl]butyric acid methyl ester (110 mg, 0.35 mmol) was dissolved in 5 mL of methylene chloride. Triethylamine (144 µL, 1.05 mmol) and chloroacetone (138 µL, 1.75 mmol) were added. The reaction was stirred overnight. The solvent was evaporated and the residue was purified by column chromatography (methylene chloride/diethyl ether: 1:3) to give 4-{4'-[3"-(2'"-oxopropylsulfanyl)butyl]phenyl-carbamoyl}butyric acid methyl ester (106) (92 mg, yield 72%).

7. 4-{4'-[3"-(2'"-oxopropyl-3'"-sulfonyl)butyl] phenylcarbamoyl}butyric acid methyl ester (107): 4-{4'-[3"-(2'"-Oxopropylsulfanyl)butyl]phenylcarbamoyl}butyric acid methyl ester (128 mg, 0.25 mmol) was dissolved in 3 mL of methylene chloride. At 0° C., mCPBA (87 mg, 0.25 mmol) in 2 mL of methylene chloride was slowly added to the above solution. After two and half hours, the solvent was partly evaporated and the reaction mixture was diluted with 15 mL of ethyl acetate. Then the reaction mixture was washed with 10 mL of sodium bicarbonate (1.0 M). The organic phase was dried over magnesium sulfate. Evaporation of solvent followed by column chromatography (methylene chloride/diethyl ether: 1:3) to afford 4-{4'-[3"-oxopropyl-3'"-sulfonyl)butyl]phenylcarbamoyl}butyric acid methyl ester (107) (100 mg, yield 91%).

8. 4-{4'-[3"-(2'",4'"-Dioxopentane-3'"-sulfonyl)butyl] phenylcarbamoyl}butyric acid methyl ester(108): To the mixture of acetic acid (4.7 mg, 0.08 mmol, 1.2 eq) and β-diketone sulfone 107 (26 mg, 0.07 mmol) in 2 mL of dried dimethylformamide was DEPC (13 mg, 0.08 mmol, 1.2 eq), followed by addition of triethylamine (21 mg, 0.21 mmol, 3.2 eq). The reaction mixture was stirred at 0° C. for 2 h, and then at room temperature for 20 h. After evaporation of the solvent, the residue was dissolved in benzene-ethyl acetate (1/1) (25 mL) and washed with 10% aq. sulfuric acid (10 mL) and 5% aq. sodium bicarbonate (15 mL). The organic phase was dried over sodium sulfate. Evaporation of solvent gave the crude product which was purified by column chromatography (hexane/ethyl acetate: 4/1) to afford 18 mg of β-diketone sulfone 108 with a yield 74%.

$^1$H NMR (300 Hz, CDCl$_3$): δ7.81 (s, 1 H), 7.34 (d, J=8.7 Hz, 2 H), 7.00 (d, J=8.7 Hz, 2 H), 3.61 (s, 3 H), 2.88 (m, 1 H), 2.63 (t, J=7.3 Hz, 2 H), 2.51 (d, J=7.3 Hz, 2 H), 2.39 (t, J=7.1 Hz, 2 H), 2.10 (pent, J=7.3 Hz, 2 H), 2.05 (s. 6 H), 1.80

(m, 2 H), 1.30 (d, J=7.1 Hz, 3 H); MS m/z: 462 (M+Na$^+$, 82%), 440 (M+H$^+$, 53%); C$_{21}$H$_{29}$O$_7$NS (439.52).

9. 4-{4'-[3"-(2'",4'"-Dioxopentane-3'"-sulfonyl)butyl] phenylcarbamoyl}butyric acid (109): β-diketone sulfone 108 (18 mg, 0.041 mmol) was added to 2 mL of lithium hydroxide solution (30 mM). The reaction mixture was stirred for 2 h at room temperature, then it was acidified by 1 M aqueous hydrochloric acid. β-diketone sulfone hapten 109 was isolated by extraction with ethyl acetate. There was obtained 16 mg of β-diketone sulfone hapten 109 for a yield of 92%.

$^1$H NMR (300 MHz, CDCl$_3$): δ7.88 (s, 1 H), 7.44 (d, J=9.0 Hz, 2 H), 6.99 (d, J=9.0 Hz, 2 H), 2.87 (m, 1 H), 2.62 (t, J=7.2 Hz, 2H), 2.50 (d, J=7.2 Hz, 2H), 2.41 (t, J=7.3 Hz, 2 H), 2.10 (pent, J=7.2 Hz, 2 H), 2.02 (s, 6 H), 1.77 (m, 2 H), 1.29 (d, J=7.3 Hz, 3 H); MS m/z: 426 (M+H$^+$, 98%); C$_{30}$H$_{27}$O$_9$NS (425.50).

10. 4-{4'-[3"-(2'",4'"-Dioxopentane-3'"-sulfonyl)butyl] phenylcarbamoyl}butyric acid N-succinimoyl ester (110): β-diketone sulfone hapten 109 (18 mg, 0.037 mmol), DCC (11 mg, 0.052 mmol) and N-hydroxysuccinimide (2.5 mg, 0.052 mmol) were added to 3 mL of 1,4 dioxane under nitrogen. The reaction mixture was stirred at room temperature (it was a clear solution) for overnight. Then the reaction mixture was filtered, washed with 3×20 mL of diethyl ether. The solvent of ethereal solution was evaporated under vacuum. The crude product was obtained, which was further purified by column chromatography (ethyl acetate/hexane:4/1) on silica gel to give 16 mg pure activated ester 110, with a yield of 86%.

$^1$H NMR (300 MHz, CDCl$_3$); δ7.82 (s, 1 H), 7.33 (d, J=9.0 Hz, 2 H), 7.01 (d, J=9.0 Hz, 2 H), 2.88 (m, 1 H), 2.80 (s, br, 4 H), 2.62 (t, J=7.3 Hz, 2 H), 2.50 (d, J=7.3 Hz, 2 H), 2.50 (d, J=7.3 Hz, 2 H), 2.38 (t, J=7.2 Hz, 2 H), 2.11 (pent, J=7.3 Hz, 2 H), 2.04 (s, 6 H), 1.82 (m, 2 H), 1.31 (d, J=7.2 Hz, 3 H); MS (electorspray) m/z: pos. 531 (M+Na$^+$, 44%), 509 (M+H$^+$, 76%); C$_{24}$H$_{30}$O$_9$NS (508.56).

What is claimed is:

1. A hybridoma having ATCC accession number PTA-1015 which is capable of expressing antibody 85A2.

2. A hybridoma having ATCC accession number PTA-1014 which is capable of expressing antibody 85C7.

3. A hybridoma having ATCC accession number PTA-1017 which is capable of expressing antibody 92F9.

4. A hybridoma having ATCC accession number PTA-1018 which is capable of expressing antibody 84G11.

5. A hybridoma having ATCC accession number PTA-1019 which is capable of expressing antibody 84H9.

6. A hybridoma having ATCC accession number PTA-1016 which is capable of expressing antibody 90G8.

* * * * *